(12) United States Patent
Tanaka et al.

(10) Patent No.: US 8,041,514 B2
(45) Date of Patent: *Oct. 18, 2011

(54) METHOD FOR JUDGING FEATURE OF MALIGNANT TUMOR

(75) Inventors: Satoshi Tanaka, Kobe (JP); Masaki Shibayama, Kobe (JP); Hideki Ishihara, Miki (JP); Tomoko Matsushima, Kobe (JP); Aya Katayama, Kakogawa (JP); Yuko Kawasaki, Kobe (JP)

(73) Assignee: Sysmex Corporation, Hyogo (JP)

( * ) Notice: Subject to any disclaimer, the term of this patent is extended or adjusted under 35 U.S.C. 154(b) by 1238 days.

This patent is subject to a terminal disclaimer.

(21) Appl. No.: 11/711,053

(22) Filed: Feb. 27, 2007

(65) Prior Publication Data

US 2007/0202555 A1   Aug. 30, 2007

(30) Foreign Application Priority Data

Feb. 28, 2006   (JP) .................................. 2006-053945
Dec. 22, 2006   (JP) .................................. 2006-345880

(51) Int. Cl.
G01N 33/574   (2006.01)
G06F 19/00   (2006.01)

(52) U.S. Cl. ........................................ 702/19; 435/7.23

(58) Field of Classification Search .......................... None
See application file for complete search history.

(56) References Cited

U.S. PATENT DOCUMENTS 6,193,654 B1 *   2/2001   Richardson et al. .......... 600/300

FOREIGN PATENT DOCUMENTS

| EP | 1 600 513 A1 | 11/2005 |
| EP | 1 686 377 A1 | 8/2006 |
| EP | 1 750 131 A1 | 2/2007 |
| EP | 1 764 615 A1 | 3/2007 |
| WO | WO 2005/020794 A2 | 3/2005 |

OTHER PUBLICATIONS

Ishihara et al. (Biochimica et Biophysica Acta, 2005, 1741, 226-233).*
Kumar-Sinha et al. (Urology, 2003, 62(Suppl 6b), 19-35).*
Dosaka-Akita et al. (Cancer Research, 2001, 61, 2500-2504).*
Ross et al. (Proceedings of the American Association for Cancer Research, 1997, 38, 277, #1862).*

(Continued)

*Primary Examiner* — Marjorie Moran
*Assistant Examiner* — Larry D Riggs, II
(74) *Attorney, Agent, or Firm* — Sughrue Mion, PLLC (57) ABSTRACT

A method for judging feature of malignant tumor is described. The method comprises obtaining step, first comparing step, second comparing step and judging step. The obtaining step comprises obtaining a first parameter based on activity and expression level of a first cyclin dependent kinase (first CDK) contained in a tumor cell of the malignant tumor, a second parameter based on activity and expression level of a second cyclin dependent kinase (second CDK) contained in the tumor cell, a third parameter based on the first parameter and the second parameter, and a fourth parameter based on expression level of a cyclin contained in the tumor cell. The first comparing step comprises comparing a first threshold value with the third parameter. The second comparing comprises comparing a second threshold value with the fourth parameter. The judging step comprises judging the feature of the malignant tumor based on the comparison results of the first comparing step and the second comparing step.

11 Claims, 1 Drawing Sheet

OTHER PUBLICATIONS

Kim, J. H., et al, "Amplified CDK2 and cdc2 Activities in Primary Colorectal Carcinoma", Cancer, American Cancer Society, Philadephia, PA, US, vol. 85, No. 3, Feb. 1, 1999, pp. 546-553, XP002979096.

Kim, S. J., et al, "Prognostic significance of CDKs profiling in breast cancer", Breast Cancer Research and Treatment, vol. 94, No. Suppl. 1, 2005, pp. S128-S129, XP002438136.

Li, K. K. W., et al, "Activation of cyclin-dependent kinases CDC2 and CDK2 in hepatocellular carcinoma", Liver, Copenhagen, DE, vol. 22, 2002, pp. 259-268, XP002979097.

Khandan Keyomarsi, Ph.D., et al., "Cyclin E and Survival in Patients With Breast Cancer", The New England Journal of Medicine, Nov. 14, 2002, pp. 1566-1575, vol. 347, No. 20, Massachusetts Medical Society, www.nejm.org.

Hisanori Kawamoto, et al., "Short Communication", American Journal of Pathology, 1997, pp. 15-23, vol. 150, No. 1, American Society for Investigative Pathology.

* cited by examiner

METHOD FOR JUDGING FEATURE OF MALIGNANT TUMOR

BACKGROUND OF THE INVENTION

1. Field of the Invention

The present invention relates to a method for judging a feature of a malignant tumor based on an analysis result obtained through analysis of protein of a tumor cell of the malignant tumor collected from a patient.

2. Description of the Related Art

It is conventionally known that feature of malignant tumor can be judged when an expression level of cyclin of malignant tumor cell is measured.

For example, according to the literature by Keyomarsi K. et al. (The New England Journal of Medicine, vol. 347, No. 20, 2002, pages 1566-1575), an expression level of cyclin E is used in the prognosis of breast cancer. The literature by Keyomarsi K. reports that the expression level of the cyclin E in the tumor cell obtained from a breast cancer patient is measured, and a survival rate is low when the expression level of the cyclin E is high, in other words, a poor prognosis is exhibited. However, the malignant tumor in which the expression level of the cyclin E is low may be recurrent in some cases. Therefore, prognosis of the malignant tumor and judgment of a risk of recurrence thereof based on the expression level of the cyclin E is not accurate enough.

Further, according to the literature by Hisanori Kawamoto and colleagues (American Journal of Pathology, vol. 150, No. 1, 1997, pages 15-23), expression levels of a cyclin B1 and CDK1 in nonmalignant and malignant human breast lesions are measured. The literature by Hisanori Kawamoto and colleagues reports that the benign/premalignant lesions and the breast carcinomas can be discriminated from each other when the expression levels of the cyclin B1 and CDK1 are used. However, the relevant literature merely reporting the measurement of the expression levels of the cyclin B1 and CDK1 fails to include any recitation relating to a method for judging the feature of the malignant tumor such as the risk of recurrence thereof.

SUMMARY OF THE INVENTION

The scope of the present invention is defined solely by the appended claims, and is not affected to any degree by the statements within this summary.

A main object of the present invention is to provide a method for judging a feature of a malignant tumor with a high accuracy based on an analysis result obtained through analysis of molecules expressed in a tumor cell of the malignant tumor collected from a patient.

A first aspect of the present invention relates to method for judging feature of malignant tumor, comprising the steps of:

obtaining a first parameter based on activity and expression level of a first cyclin dependent kinase (first CDK) contained in a tumor cell of the malignant tumor, a second parameter based on activity and expression level of a second cyclin dependent kinase (second CDK) contained in the tumor cell, a third parameter based on the first parameter and the second parameter, and a fourth parameter based on expression level of a cyclin contained in the tumor cell;

first comparing a first threshold value with the third parameter;

second comparing a second threshold value with the fourth parameter;

judging the feature of the malignant tumor based on the comparison results of the first comparing step and the second comparing step.

A second aspect of the present invention relates to method for judging risk of recurrence of malignant tumor, comprising steps of:

obtaining a first parameter based on activity and expression level of a first cyclin dependent kinase (first CDK) contained in a tumor cell of the malignant tumor, a second parameter based on activity and expression level of a second cyclin dependent kinase (second CDK) contained in the tumor cell, a third parameter based on the first parameter and the second parameter, and a fourth parameter based on expression level of a cyclin contained in the tumor cell;

first comparing a first threshold value with the third parameter;

first classifying the malignant tumor into one of Group A and Group X having a risk of recurrence higher than that of the Group A based on a comparison result of the first comparing step;

second comparing a second threshold value with the fourth parameter when it is judged that the malignant tumor is included in the Group X; and second classifying the Group X into Group B and Group C having the risk of recurrence higher than that of the Group B based on a comparison result of the second comparing step.

A third aspect of the present invention relates to a computer program product for enabling a computer to execute a method of a method for judging feature of malignant tumor, the computer program product comprising:

a computer readable medium; and software instructions, on the computer readable medium, for enabling the computer to perform predetermined operations comprising:

obtaining a first parameter based on activity and expression level of a first cyclin dependent kinase (first CDK) contained in a tumor cell of the malignant tumor, a second parameter based on activity and expression level of a second cyclin dependent kinase (second CDK) contained in the tumor cell, a third parameter based on the first parameter and the second parameter, and a fourth parameter based on expression level of a cyclin contained in the tumor cell;

first comparing a first threshold value with the third parameter;

second comparing a second threshold value with the fourth parameter;

judging the feature of the malignant tumor based on the comparison results of the first comparing step and the second comparing step.

DESCRIPTION OF THE PREFERRED EMBODIMENTS

A judging method according to a preferred embodiment of the present invention judges feature of malignant tumor obtained from a patient by using a first CDK, a second CDK and cyclin in a tumor cell of the malignant tumor. According to the method wherein a result of analyzing expression levels and activity values of the plurality of CDKs and an expression level of the cyclin expressed in the tumor cell obtained from the patient is used, the feature of the malignant tumor can be accurately judged.

A method for judging feature of malignant tumor according to a preferred embodiment of the present invention includes steps of:

obtaining a first parameter based on an activity value and an expression level of a first cyclin-dependent kinase (first CDK) contained in a tumor cell of the malignant tumor, a second parameter based on an activity value and an expression level of a second cyclin-dependent kinase (second CDK) contained in the tumor cell, a third parameter based on the first and second parameters, and a fourth parameter based on an expression level of cyclin contained in the tumor cell;

first comparing the third parameter to a first threshold value;

second comparing the fourth parameter to a second threshold value; and judging the feature of the malignant tumor based on comparison results obtained from the first and second comparison steps.

Examples of the malignant tumor recited in this specification include malignant tumor derived from a hematopoietic organ, carcinoma derived from an epithelial cell, sarcoma and the like. Examples of the malignant tumor derived from the hematopoietic organ include leukemia, malignant lymphoma and the like. Examples of the carcinoma include breast cancer, stomach cancer, large intestine cancer, esophagus cancer, prostate cancer and the like. Examples of the sarcoma include osteogenic sarcoma, sarcoma on soft parts and the like.

The tumor cell whose feature is to be judged is preferably a tumor cell of early stage carcinoma. The early stage carcinoma recited in this specification refers to cancer judged to be in stages I and IIA in a stage classification.

The stage classification shows the malignancy of the malignant tumor. A method for the classification is different depending on the type of the malignant tumor. For example, in the case of the breast cancer, there are stages, in the lower order of the malignancy, 0-IV. The stage II is generally classified, in the lower order of the malignancy, into the stage IIA and the stage IIB, and the stage III is classified, in the lower order of the malignancy, into the stage IIIA and the stage IIIB. The stage classification is based on the TNM classification. The TNM classification is a stage classification of the malignant tumor by the Union Internationale Contra le Cancer (UICC). "T" denotes a size of a primary tumor, and the primary tumor is classified into T0 (primary lesion cannot be confirmed)-T4 (tumor is exposed out of body). "N" denotes a degree of invasion into lymphonodus in vicinity, and the tumor is classified into N0 (metastasis into the lymphonodus is not detected)-N3 (metastasis into the lymphonodus near the median eminence of the body (lymphonodus in vicinity of breast bone) is suspected). "M" denotes presence or absence of distant metastasis, and the tumor is classified into M0 (no distant metastasis) and M1 (distance metastasis is detected).

In the case of the breast cancer, the malignant tumor in the stage I indicates the malignant tumor in "T1, N0, M0" in the TNM classification. The malignant tumor in the stage IIA indicates the malignant tumor in "T0, N1, M0", "T1, N1, M0" or "T2, N0, M0" in the TNM classification. The malignant tumor in the stage IIB indicates the malignant tumor in "T2, N1, M0" or "T3, N0, M0" in the TNM classification.

Examples of the feature of the malignant tumor to be judged by means of the judging method include a proliferation potency and risk of recurrence (likelihood of transfer) of the tumor cell and the like. The judging method is particularly preferably used for the judgment of the risk of recurrence. The recurrence means that after a certain period has passed after the treatment of the tumor (extraction, treatment by carcinostatic, hormone therapy and the like), the recurrence of the malignant tumor is detected in the same part and the tumor cell is separated from the primary lesion and carried into a distant tissue to independently propagate. The possibility of the recurrence is judged based on the proliferation potency, survival potency, migratory aptitude and the like of the tumor cell.

The method for judging the feature of the malignant tumor according to the preferred embodiment includes the parameter obtaining step for obtaining the respective parameters, first comparison step, second comparison step and judging step.

Parameter Obtaining Step

In the parameter obtaining step, the first parameter based on the first CDK contained in the tumor cell, the second parameter based on the second CDK contained in the tumor cell, the third parameter obtained from the first and second parameters and the fourth parameter obtained from the expression level of the cyclin contained in the tumor cell are obtained.

The CDK is a collective term of enzymes activated through binding of protein called the cyclin and functions in a particular stage of a cell cycle depending on the type thereof. As the types of the CDK can mentioned CDK1, CDK2, CDK3, CDK4, CDK5, CDK6, CDK7 and the like. In the present preferred embodiment, the CDKs of at least the two types (first CDK and second CDK) are used, and two CDKs selected from a group consisting of CDK1, CDK2, CDK4 and CDK6 are preferably combined and used because the CDK1, CDK2, CDK4 and CDK6 directly relate to the transition of the stage of the cell cycle. For example, a complex consisting of the CDK4 or CDK6 and cyclin D triggers the transition from stage G1 to stage S of the cell cycle, which generates the activation of a complex consisting of the CDK2 and cyclin E, and the cell really enters the stage S. After that, a complex consisting of the CDK2 and cyclin A is activated, and the cell thereby shifts from the stage S to stage G2. Then, a complex consisting of the CDK1 and cyclin B is activated, and the cell can thereby proceed to stage M. Further, the combination of the CDK1 and CDK2 is preferably used. More specifically, the first CDK is preferably CDK1, and the second CDK is preferably CDK2.

The first parameter is a parameter obtained from the activity value and the expression level of the first CDK, and the second parameter is a parameter obtained from the activity value and the expression level of the second CDK. As these parameters, one of the activity value and the expression level may be solely used, or a value calculated through addition, subtraction, multiplication or division of the activity value and the expression level may be used. A ratio between the activity value and the expression level is preferably used. As the ratio between the activity value and the expression level, a value obtained by dividing the activity value by the expression level (specific activity), a value obtained by dividing the expression level by the activity value (inverse number of the specific activity), or the like, can be used.

The third parameter is a parameter obtained based on the first and second parameters. A value obtained through addition, subtraction, multiplication or division of the first and second parameters can be used as the third parameter, and a ratio between the first and second parameters is preferably used. As the ratio between the first and second parameters, a value obtained by dividing the first parameter by the second parameter, a value obtained by dividing the second parameter by the first parameter, or the like, can be used.

The cyclin is a type of protein known as a cell cycle-related protein, and constitutes an adjustment subunit of protein phosphorylation enzyme such as CDK. The types of the cyclin are cyclin A, cyclin B, cyclin C, cyclin D, cyclin E, cyclin H, cyclin K, cyclin T and the like. A cyclin capable of constituting a complex with the first CDK or the second CDK is preferably used as the cyclin to be used. More specifically, a cyclin capable of constituting a complex with the CDK selected from a group consisting of the CDK1, CDK2, CDK4 and CDK6 is preferably used based on the reason described earlier, examples of which are the cyclin A, cyclin B, cyclin D, cyclin E. Of these examples, the cyclin B or the cyclin E is more preferably used. The cyclin B recited in this specification includes cyclin B1, cyclin B2 and the like. The cyclin E recited in this specification includes cyclin E1, cyclin E2 and the like.

The fourth parameter is a parameter obtained from the expression level of the cyclin. A value calculated thorough addition, subtraction, multiplication or division of the expression level and the activity value of the cyclin may be used as the fourth parameter, and the expression level is preferably solely used.

First Comparison Step

In the first comparison step, the third parameter is compared to the corresponding threshold value (hereinafter, referred to as first threshold value).

The first threshold value is appropriately set depending on what type of feature of the tumor cell is judged. In the case of judging the risk of recurrence of the tumor cell, for example, of breast cancer cells obtained from a plurality of patients, the third parameter is calculated with respect to a cell whose recurrence or non-recurrence in five years after the extirpative surgery is already known. Then, a value capable of separating the group of patients into a high-value group (group in which the risk of recurrence is high) and a low-value group (group in which the risk of recurrence is low) at a predetermined separation ratio when the calculated values of the third parameters are arranged from the smaller value can be used as the first threshold value. In the case of the breast cancer, for example, the separation ratio of the high-value group is preferably at least 30% of the group of patients since the rate of recurrence in five years after the extirpative surgery is approximately 30%, and is more preferably a ratio higher than 30% in order to eliminate the possibility that the patients classified into the low-value group undergo the recurrence. More specifically, as the first threshold value, such values that the ratio of the group of patients classified into the high-value group and the low-value group is 30:70, preferably 40:60 and more preferably 50:50 (median) or 60:40 can be used. The separation ratio is not necessarily strictly set because it is possible that such values that can accurately separate the group of patients at the ratio of 50:50 or 60:40 do not exist. For example, in the case where the number of the patients constituting the group of patients is 99, a value which can separate the group of patients at the ratio of 50:50 does not exist, in which case the separation ratio may be set to 50:49.

Depending on the tumor cell, the first parameter or the second parameter, or the both parameters may have very small values or very large values, and the third parameter thereby may show a value significantly different to the first threshold value. In such a case, a threshold value is preferably set for the first parameter and the second parameter besides the first threshold value. More specifically, the first comparison step may comprises the comparison of the first parameter to the corresponding threshold value, comparison of the second parameter to the corresponding threshold value, and comparison of the third parameter to the first threshold value. For example, when the first parameter is below the corresponding threshold value and the second parameter is below the corresponding threshold value, the risk of recurrence may be judged as low irrespective of the result of the comparison of the third parameter to the first threshold value. When the second parameter is at least the corresponding threshold value, the risk of recurrence may be judged as high irrespective of the result of the comparison of the third parameter to the first threshold value.

When a value of the ratio between the first parameter and the second parameter is used as the third parameter, the denominator may be zero. In such a case, the value of the ratio cannot be calculated. Therefore, the value can be handled as infinity, which is interpreted as equal to or above the first threshold value.

Second Comparison Step

In the second comparison step, the fourth parameter is compared to the threshold value corresponding thereto (hereinafter, referred to as second threshold value).

The second threshold value is appropriately set depending of what type of feature of the tumor cell is judged. For example, in the case of judging the risk of recurrence of the tumor cell, the second threshold value which is coincident with the actual recurrence or non-recurrence at a high rate when the risk of recurrence of the tumor cell whose recurrence non-recurrence after a predetermined period has passed is known is judged in combination with the result of the first comparison step.

Either of the first and second comparison steps may be executed first as far as it is executed before the judging step.

Measurement of Activity Value/Expression Level

A measurement sample used in the measurement of the activity value and the expression level can be prepared from the malignant tumor cell obtained from the patient. A method for preparing the sample is not particularly limited as far as the predetermined parameters of the CDK and cyclin can be measured. For example, a sample in which the cell is solubilized (hereinafter, referred to as cell lysate) can be used as the measurement sample. The cell lysate is prepared in such a manner that a buffer solution including a surface active agent is added to the tumor cell obtained from the patient so that the tumor cell is physically and/or chemically ground in the buffer solution. As a result of the process, protein such as the CDK and cyclin contained in the cell are liberated in the solution. The cell lysate is centrifuged so that the supernatant including the CDK and the cyclin is obtained, and the obtained supernatant can be used as the measurement sample.

A method for the measuring the activity value of the CDK is not particularly limited, and any conventional method can be used for the measurement. For example, a method in which 32P-labeled ATP ($\gamma$-(32P)-ATP) is used can be mentioned as an example. According to the method, the measurement sample, a substrate and $\gamma$-(32P)-ATP are mixed so that 32P is introduced into the substrate by the actions of these kinases. Next, a labeling amount of the phosphorylated substrate labeled with 32P is measured, and the phosphorylated substrate is determined based on an analytical curve generated by a calibrator. Then, the activity values of kinases are calculated based on the determined amount of the phosphorylated substrate.

Alternatively, a method recited in the U.S. Patent Application Publication No. 2002-0164673 can be used as a method in which a radioactive material is not used. According to the method, a sample including any or both of these kinases, a substrate and adenosine 5'-O-(3-thiotriphosphate) (ATP-$\gamma$S)

are mixed, and a monothiophosphoric group is introduced into the substrate by the actions of the kinases. A labeled fluorescent material or a labeled enzyme is combined with a sulfur atom of the introduced monothiophosphoric group so that the substrate is labeled, a labeling amount of the labeled monothiophosphorylated substrate is measured, and the monothiophosphorylated substrate is determined based on the analytical curve generated by the calibrator. The activity values of the kinases are calculated based on the determined amount of the monothiophosphorylated substrate. A sample kit provided with a reagent including an anti-CDK antibody, a reagent including the CDK substrate, a reagent including ATP-γS and a reagent including a labeled material which can be combined with the phosphorylated substrate can be used for the measurement. The CDK substrate and ATP-γS may be housed in a same container.

A method for measuring the expression levels of the CDK and cyclin is not particularly limited, and any conventional method can be used for the measurement. For example, ELISA, western blotting, a method recited in the U.S. Patent Application Publication No. 2004-0214180 and the like can be used for the measurement of the measurement sample so that the expression levels of the CDK and cyclin can be obtained. In the case where the method recited in the U.S. Patent Application Publication No. 2004-0214180 is adopted, the expression levels of the CDK and cyclin can be measured according to the following method.

First, the measurement sample is made to contact a solid phase so that the CDK or the cyclin in the measurement sample is combined with the solid phase in the measurement sample. Next, an antibody which is labeled or has a part reactive to the label and is specific to the CDK or the cyclin is combined with the CDK or the cyclin. In the case where an unlabeled antibody is used, the label is made to act on a part reactive to the label so that the antibody is labeled. Then, an amount of the label combined with the CDK or the cyclin is measured. The expression level of the CDK or the cyclin is measured by means of the labeling amount based on the previously prepared analytical curve.

In the measurement sample which is prepared from the tumor cell obtained from the patient, number of tumor cells is different in each measurement sample. Therefore, the expression level of protein such as the cyclin shows different measurement values depending on the number of the tumor cells contained in the measurement sample. Accordingly, the measured value of the expression level is preferably corrected. When the measured value of the expression level is corrected, an expression level of protein coded by a housekeeping gene, (hereinafter, referred to as housekeeping protein), for example, can be used for the correction. The housekeeping protein shows a substantially constant expression level in any cell, examples of which are glyceraldehyde-3-phosphoric dehydrogenation enzyme (GAPDH), actin and the like. More specifically, not only the expression level of the protein in the measurement sample but also the expression level of the housekeeping protein is measured, and the expression level of the protein in the measurement sample is divided by the expression level of the housekeeping protein so that the measured value of the expression level can be corrected. In the case where the expression level or the ratio between the activity value and the expression level is used as the first parameter, the expression level or the ratio between the activity value and the expression level is used as the second parameter, and the ratio between the first and second parameters is used as the third parameter, the expression levels of the first CDK and the second CDK are measured; however, the expression level of the housekeeping protein is offset in the calculation, which makes the foregoing correction unnecessary.

Judging Step

In the judging step, the feature of the malignant tumor is judged based on the comparison result of the first comparison step and the comparison result of the second comparison step. As described, the third parameter is obtained from the activity value and the expression level of the first CDK and second CDK, and the fourth parameter is obtained from the expression level of the cyclin.

For example, when the risk of recurrence is predicted as the feature of the malignant tumor, the malignant tumor can be classified into any of three groups respectively having the recurrence risks of different degrees (for example, high, intermediate and low) based on these results. As specific example of the method, any of methods 1-5 described below can be used, so that the risk of recurrence can be judged.

In the method 1, the result of the comparison of the third parameter to the first threshold value and the result of the comparison of the fourth parameter to the second threshold value are combined so that the risk of recurrence is judged. When the respective parameters are below the threshold values in both of the comparison results, the risk of recurrence is judged as low and classified into "Group A1". When one of the parameters is at least the threshold value, and the other is below the threshold value in these comparison results, the risk of recurrence is classified into "Group B1" in which the risk of recurrence is higher than the "Group A1". When the respective parameters are at least the threshold values in both of the comparison results, the risk of recurrence is classified into "Group C1" in which the risk of recurrence is higher than the "Group B1".

There are possible cases where the different degrees of the risk of recurrence are obtained among the results classified into the "Group B1" depending on if the third parameter is at least the first threshold value or the fourth parameter is at least the second threshold value. In these cases, the case where the third parameter is at least the first threshold value may be classified into "Group B1-1", and the case where the fourth parameter is at least the second threshold value may be classified into "Group B1-2". Thereby, the malignant tumor can be classified into any of the four groups respectively representing the different degrees of the risk of recurrence.

In the method 2, when the third parameter is compared to the first threshold value and the third parameter is at least the threshold value, the classification into "Group C2" is defined. When the third parameter is below the threshold value, the classification is not defined, and the fourth parameter is compared to the second threshold value. When the fourth parameter is at least the threshold value, the relevant tumor is classified into "Group B2" in which the risk of recurrence is lower than that of the tumor classified into the "Group C2". When the fourth parameter is below the threshold value, the relevant tumor is classified into "Group A2" in which the risk of recurrence is lower than that of the tumor classified into the "Group B2".

In the method 3, when the fourth parameter is compared to the second threshold value, and the fourth parameter is at least the threshold value, the classification into "Group C3" is defined. When the fourth parameter is below the threshold value, the classification is not defined, and the third parameter is compared to the first threshold value. When the third parameter is at least the threshold value, the relevant tumor is classified into "Group B3" in which the risk of recurrence is lower than that of the tumor classified into the "Group C3".

When the third parameter is below the threshold value, the relevant tumor is classified into "Group A3" in which the risk of recurrence is lower than that of the tumor classified into the "Group B3".

In the method 4, when the third parameter is compared to the first threshold value, and the third parameter is below the threshold value, the classification into "Group A4" is defined. When the third parameter is at least the threshold value, the classification is not defined, and the fourth parameter is compared to the second threshold value. When the fourth parameter is below the threshold value, the relevant tumor is classified into "Group B4" in which the risk of recurrence is higher than that of the tumor classified into the "Group A4". When the fourth parameter is at least the threshold value, the relevant tumor is classified into "Group C4" in which the risk of recurrence is higher than that of the tumor classified into the "Group B4".

In the method 5, when the fourth parameter is compared to the second threshold value, and the fourth parameter is below the threshold value, the classification into "Group A5" is defined. When the fourth parameter is at least the threshold value, the classification is not defined. Therefore, the third parameter is compared to the first threshold value. When the third parameter is below the threshold value, the relevant tumor is classified into "Group B5" in which the risk of recurrence is higher than that of the tumor classified into the "Group A5". When the third parameter is at least the threshold value, the relevant tumor is classified into "Group C5" in which the risk of recurrence is higher than that of the tumor classified into the "Group B5".

In the methods 1-5, the Groups A, B and C respectively show the relatively different degrees of the risk of recurrence. In each of the methods 1-5, "Group A" shows that the risk of recurrence is relatively low, "Group C" shows that the risk of recurrence is relatively high, and "Group B" shows that the risk of recurrence is at an intermediate level between "Group A" and "Group C". The threshold values may be the same or different in the respective methods 1-5.

Which of the methods 1-5 is used can be decided in consideration of the types of the malignant tumor, types of the parameter, correlation with clinical data and the like. In the case of judging the risk of recurrence of the malignant tumor, any of the methods 1 and 4 is preferably used, and the method 4 is more preferably used.

In the case of using the method 1, either of the first comparison step for comparing the third parameter to the first threshold value and the second comparison step for comparing the fourth parameter to the second threshold value may be executed first as far as it is executed prior to the step of judging the risk of recurrence.

As a possible process in the case of using the methods 2-5, of the first comparison step for comparing the third parameter to the first threshold value and the second comparison step for comparing the fourth parameter to the second threshold value, one of them is executed first, and a first step of judging the risk of recurrence is executed based on the obtained comparison result. Then, only in the case where the risk of recurrence fails to be judged, the other comparison step is executed, and a second step of judging the risk of recurrence is executed based on the obtained comparison result. Accordingly, the risk of recurrence can be judged in a fewer steps. More specifically, in the method 4:

the first comparison step for comparing the third parameter to the first threshold value is executed;

the step of classifying the malignant tumor into one of the Group A4 and the other group in which the risk of recurrence is higher than in the Group A4 is executed based on the obtained comparison result;

the second comparison step for comparing the fourth parameter to the second threshold value is executed when the it is judged that the malignant tumor is included in the group in which the risk of recurrence is higher than in the Group A4; and the step of classifying the group in which the risk of recurrence is higher than in the Group A4 into the Group B4 and the Group C4 in which the risk of recurrence is higher than the Group B4 is executed based on the obtained comparison result.

Accordingly, the malignant tumor can be classified into the three groups respectively representing the different degrees of the risk of recurrence in a fewer steps.

The CDK deeply relates to the proliferation of the cell. Therefore, when the comparison step (first comparison step) in which the CDK is used is executed, the proliferation potency of the tumor cell can be accurately grasped. As described earlier, the proliferation potency of the tumor cell is a key factor affecting the risk of recurrence of the cell. Further, the cyclin, which is the cell cycle-related protein, also relates to the proliferation of the cell and is an effective factor used for the judgment of the risk of recurrence of the malignant tumor. However, the judgment of risk of recurrence thereby obtained cannot be accurate enough. When one of the first and second comparison steps is used, the malignant tumor can be classified into the two groups respectively representing the different degrees of the risk of recurrence. Further, when the method 4 according to the present preferred embodiment is used, for example, the results of these comparison steps are combined so that the group in which the risk of recurrence is judged as high based on the result of the first comparison step can be further classified into the group in which the risk of recurrence is remarkably high and the group in which a typical rate of recurrence is shown based on the result of the second comparison step. Therefore, the prognosis of the risk of recurrence of the malignant tumor can be accurate.

The result of the judgment of the feature of the malignant tumor thus far described can be an indicator for the selection of a therapeutic method. For example, it can help decide if such an aggressive therapy as chemotherapy (therapy in which carcinostatic is used), such a less aggressive therapy as a hormone therapy, or the like, should be selected for the patient suffering the malignant tumor. A type and an amount of the therapeutic drug to be administered can be adjusted based on the judgment result.

The method according to the present preferred embodiment is preferably executed as a computer program. A computer program (FIG. 1) and a judgment flow (FIG. 2) for executing the method are described below.

Figure 1:
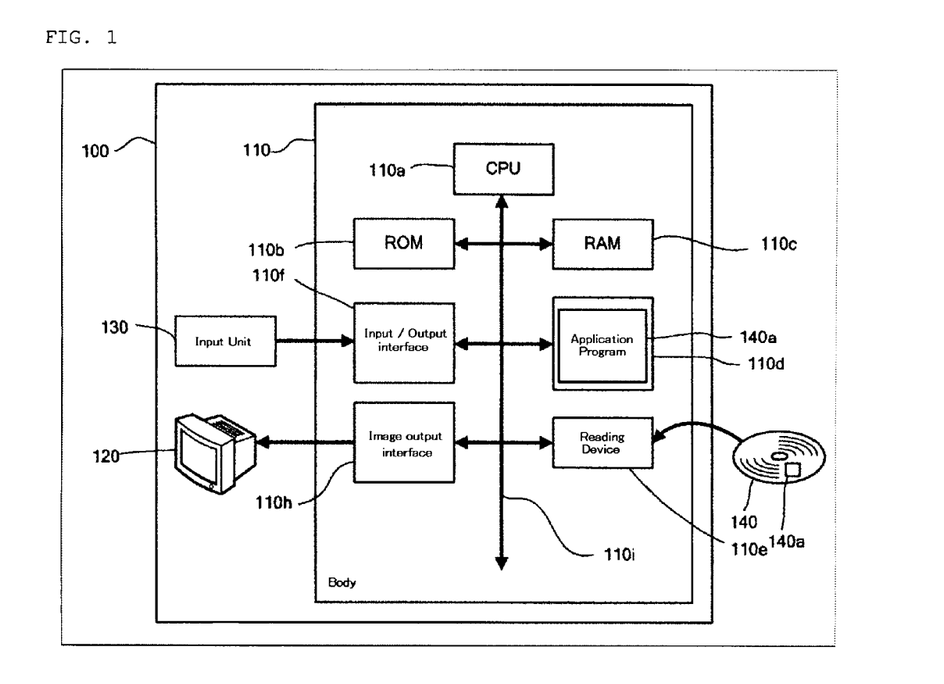
FIG. 1 is a block diagram showing the structure of the computer system 100.

A system 100 shown in FIG. 1 comprises a body 110, an input unit 130 for inputting necessary data to the body 110, and a display 120 for displaying input and output data and the like, and may further include a portable recording medium 140 if necessary. A program 140*a* according to the present preferred embodiment may be recorded on the portable recording medium 140, or stored in memories 110*b*-110*d* provided in the body 110. In the body 110, a CPU 110*a*, the memories 110*b*-110*d*, an input/output interface 110*f*, an image output interface 110*h*, and a reading device 110*e* are connected via a bus 110*i* so that data can be transmitted and received.

Figure 2:
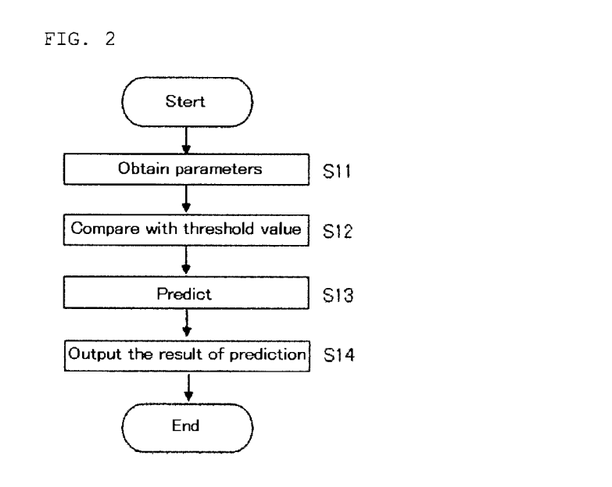
FIG. 2 is a flow chart illustrating a processing sequence of a computer program for executing the method 3 according to a preferred embodiment of the present invention.

FIG. 2 is a flow chart illustrating a processing sequence of the computer program for judging the risk of recurrence according to the method 1, and the program is stored in the memory 110d.

When the ratio between the CDK2 specific activity and the CDK1 specific activity (CDK2 specific activity/CDK1 specific activity: third parameter) and the expression level of the cyclin (fourth parameter) of a specimen are inputted from the input unit 130, the CPU 110a obtains these parameter data via the input/output interface 110f and stores the obtained data in a RAM 110c (step S11).

The CPU 110a previously reads the threshold value corresponding to the third parameter and the threshold value corresponding to the fourth parameter stored in the memory 110d as the program data, and compares the parameter data to these threshold values (Step S12).

Next, the CPU 110a predicts and judges the risk of recurrence based on the comparison results (Step S13). The CPU 110a judges the "High" risk of recurrence when the third parameter is at least the threshold value and the fourth parameter is at least the threshold value. The CPU 110a judges the "Intermediate" risk of recurrence when the third parameter is at least the threshold value and the fourth parameter is below the threshold value. The CPU 110a judges the "Intermediate" risk of recurrence when the third parameter is below the threshold value and the fourth parameter is at least the threshold value. The CPU 110a judges the "Low" risk of recurrence when the third parameter is below the threshold value and the fourth parameter is below the threshold value.

Then, the CPU 110a stores the judgment result in the RAM 110c and outputs the judgment result to the display 20 via the image output interface 110h (Step S14).

In the present preferred embodiment, the respective parameter data, activity value, expression level and the like are inputted via the input unit 130; however, the input method is not limited thereto. For example, the data is not necessarily inputted by an operator, and the respective parameter data, activity value, expression level and the like may be automatically obtained from a measuring device via the input/output interface 110f. Further, the value of the CDK2 specific activity/CDK1 specific activity is inputted as the third parameter, As an alternative method, the expression levels and the activity values of the CDK1 and CDK2 is inputted, and the value of the CDK2 specific activity/CDK1 specific activity is calculated from these values by the CPU 110a from these values, so that the obtained value can be used for the comparison to the threshold value.

Example 1

1) Preparation of Measurement Sample 51 specimen of tumor cell blocks obtained from 51 breast cancer patients (patients 1-51) classified into the stage I or the stage IIA in the breast cancer stage classification were used to prepare measurement samples 1-51 according to the following steps (the stage classification of the patients are shown in the following Table 1).

First, a buffer solution A (0.1 w/v % of Nonidet P-40 (Calbiochem Corporation), 50 mM of tris hydrochloric acid (pH 7.4), 5 mM of EDTA, 50 mM of sodium fluoride, 1 mM of sodium orthovanadate, and 100 µl/ml of protease inhibitor cocktail (including Sigma-Aldrich Corporation) and the tumor cell block was housed in a tube so that the tumor cell block in the buffer solution was approximately 150 mg/ml.

The tumor cell block was homogenized in the buffer solution A by means of an electric homogenizer, and the tumor cells were fragmented so that the cell lysate was prepared.

Next, the cell lysate was centrifuged for five minutes at 4° C. and 15,000 rpm, and the supernatant thereby obtained was used as the measurement sample.

2) Measurement of Expression Levels of Cyclin E and GAPDH

The measurement sample in which protein is included by 15 µg and a SDS loading buffer (including 200 mM of tris hydrochloric acid (pH 6.8), 40% of glycerol, 8% of SDS and 10% of 2-melcaptoethanol) in an amount ⅓ of the measurement sample were mixed and heated for five minutes at 100° C.

The heated measurement sample was used for SDS-PAGE, and a gel was dipped in a transfer buffer (including 39 mM of glycin, 40 mM of tris, 0.1% of SDS and 20% of methanol) at room temperature for 15 minutes and equilibrated.

The Mini Trans-Blot cell transfer system (Bio-Rad Laboratories, Inc.) was used so that the protein in the gel was transferred onto the Immobilon FL membrane at 100V and 4° C. for an hour (Millipore Corporation).

The membrane was blocked for one hour at 37° C. by a blocking reagent A (product name: BlockAce by Dainippon Pharmaceutical Co. Ltd.), and then, washed with a washing solution A (including 25 mM of tris hydrochloric acid (pH 7.4), 150 mM of NaCl and 0.02% of Tween 20).

After the washing, 5 ml of a mouse anti-cyclin E antibody (clone HE) (primary antibody: Santa Cruz Biotechnology, Inc.) solution which is specifically combined with the Cyclin E (clone HE) was blotted onto the membrane so that the cyclin in the membrane and the primary antibody were reacted with each other.

The membrane was washed with 20 ml of the washing solution A, and then, 5 ml of a horseradish peroxidase (HRP) labeled rabbit anti-mouse IgG (secondary antibody: Dako Ltd.) solution was blotted thereonto so that the primary antibody in the membrane and the secondary antibody were reacted with each other.

The membrane was washed with 20 ml of the washing solution A, and dipped in ECLplus (GE Healthcare Biosciences KK) for five minutes, and then, fluorescence detection was implemented with respect to an amount of the cyclin E adsorbed to the membrane by means of an fluorescence image analyzer, Molecular Imager FX (Bio-Rad Laboratories, Inc.).

The expression level of GAPDH was measured in experimental step similar to those of the measurement of the expression level of the cyclin E except for: a blocking regent B (including 4% of BSA, 25 mM of tris hydrochloric acid (pH 7.4), 150 mM of NaCl and 0.02% of Tween 20) was used as the blocking reagent in place of the blocking reagent A; a rabbit anti-GAPDH antibody was used as the primary antibody in place of the rabbit anti-cyclin E antibody; a biotin-labeled goat anti-rabbit antibody was used as the secondary antibody in place of the HRP-labeled rabbit anti-mouse IgG; and FITC conjugated streptavidin (Vector, Inc.) was combined with the biotin-labeled goat anti-rabbit antibody on the membrane so that the fluorescence detection was implemented in place of dipping the membrane in ECLplus.

The expression level of GAPDH was used in order to correct the measured value of the expression level of the cyclin E. The following value used as the expression level of the cyclin E is a value corrected by the expression level of GAPDH (value calculated from expression level of cyclin E/expression level of GAPDH).

The measurement result of the expression level of the cyclin E is shown in the following Table 1.

3) Measurement of Expression Levels of CDK1 and CDK2

In each well of the blotter in which a PVDF membrane (Millipore Corporation) was set, 50 µl each of the measurement samples was housed, and suction was applied from a bottom surface of the well, in other words, a rear surface of the membrane at a negative pressure of approximately 250 mmHg for approximately 30 seconds so that the protein in the measurement sample was adsorbed to the membrane.

100 µl of a washing solution B (including 25 mM of tris hydrochloric acid (pH 7.4) and 150 mM of NaCl) was housed in each well, and suction was applied at the negative pressure 500 mmHg for 15 seconds so that the membrane was washed.

After the washing, 40 µl of a blocking reagent B (including 4% of BSA, 25 mM of tris hydrochloric acid (pH 7.4) and 150 mM of NaCl) was housed in each well and left in a stationary state for 15 minutes. Then, suction was applied at the negative pressure of 500 mmHg for 15 seconds so that the membrane was blocked.

After the blocking, 40 µl of the rabbit anti-CDK1 antibody (primary antibody: Santa Cruz Biotechnology, Inc.) solution which is specifically combined with the CDK1 was housed in each well, and left in a stationary state at room temperature for approximately 30 minutes so that the CDK1 of the membrane and the primary antibody were reacted with each other. Then, suction was applied from the bottom surface of the well at the negative pressure of 500 mmHg for approximately 15 seconds.

100 µl of the washing solution B was housed in each well, and suction was applied at the negative pressure of 500 mmHg for 15 seconds so that the membrane was washed.

40 µl of a biotinylated anti-rabbit IgG-B antibody (secondary antibody: Santa Cruz Biotechnology, Inc.) solution was housed in each well, and left in a stationary state at room temperature for 30 minutes so that the primary and secondary antibodies in the membrane were reacted with each other. Then, suction was applied from the bottom surface of the well at the negative pressure of 500 mmHg for approximately 15 seconds.

100 µl of the washing solution B was housed in each well, and suction was applied at the negative pressure of 500 mmHg for 15 seconds so that the membrane was washed.

50 µl of a labeled solution including streptavidin labeled with FITC was housed in each well and left in a stationary state at room temperature for approximately 30 minutes, and a secondary antibody of the membrane was labeled with FITC. Then, suction was applied from the bottom surface of the well at the negative pressure 500 mmHg for approximately 15 seconds.

50 µl of the washing solution B was housed in each well, and suction was applied at the negative pressure of 500 mmHg for 15 seconds, which was repeated five times so that the membrane was washed.

The membrane was removed from the blotter, and washed with 20% methanol for approximately five minutes and dried at room temperature for approximately 20 minutes. Then, a fluorescence intensity of the protein adsorbed to the membrane was analyzed and measured by means of the fluorescence image analyzer, Molecular Image FX (Bio-Rad Laboratories, Inc.). The measured value was calculated based on the analytical curve.

The analytical curve was generated in such a manner that 50 µl each of solution, in which recombination CDK1s having five different concentrations were dissolved in the washing solution B including 0.005% of Nonidet P-40 and 50 µg/ml of BSA, was injected into each well processed in a manner similar to the foregoing manner, the FITC labeling was implemented in experimental steps similar to those described earlier, and the fluorescence intensity was measured so that a relationship between the fluorescence intensity and the expression level of the CDK1 was expressed.

The expression level of the CDK2 was measured in experimental steps similar to those in the measurement of the expression level of the CDK1 except for using a rabbit anti-CDK2 antibody as the primary antibody in place of the rabbit anti-CDK1 antibody.

4) Measurement of Activities of CDK1 and CDK2

500 µl of the buffer solution A was housed in a 1.5 ml Eppendorf tube, and the measurement sample was further added thereto. The measurement sample to be added was adjusted so that a total amount of the protein in the mixed liquid housed in the tube was 100 µg.

A cepharose beads coated with 2 µg of the anti-CDK1 antibody (Santa Cruz Biotechnology, Inc.) and 20 µl of protein A (Bio-Rad Laboratories, Inc.) was added thereto, and left in a stationary state at 4° C. for an hour so that the CDK1 and the anti-CDK1 antibody were reacted with each other.

After the reaction, the beads were washed, three times with a buffer solution for washing the beads (including 0.1 w/v % of Nonidet P-40 and 50 mM of tris hydrochloric acid (pH 7.0)), and suspended again in 15 µl of the buffer solution A so that the sample including the cepharose beads with which the CDK1 is combined via the anti-CDK1 antibody was obtained.

A substrate solution of the CDK1 (including 10 µg of histone H1 (Upstate Biotech, Inc.), 5 mM of ATP-γs (Sigma-Aldrich Corporation), 20 mM of tris hydrochloric acid (pH 7.4) and 0.1% of TritonX-100) was added to the sample. The substrate solution to be added was adjusted so that a total amount of the mixed liquid housed in the tube was 50 µl. The obtained solution was shaken for 10 minutes at 37° C. to generate a kinase reaction so that a monothiophosphoric group was introduced into the histone H1.

After the kinase reaction, the solution was centrifuged for 20 seconds at 2,000 rpm so that the beads were precipitated. As a result, 18 µl of the supernatant was obtained.

15 µl of a combined buffer solution (including 150 mM of tris hydrochloric acid (pH 9.2) and 5 mM of EDTA) and 10 mM of iodine acetylbiotin solution (including 100 mM of tris hydrochloric acid (pH 7.5) and 1 mM of EDTA) were added to the supernatant, and left in a stationary state at room temperature and in a dark place for 90 minutes so that the sulfur atom in the substrate into which the monothiophosphoric group is introduced (monothiophosphorylated substrate) was combined with the iodine acetylbiotin.

2-melcaptoethanol was added thereto so that the reaction between the iodine acetylbiotin and the monothiophosphoric group was halted.

The sample including 0.4 µg of the monothiophosphorylated substrate with which the iodine acetylbiotin is combined was blotted on the PVDF membrane by means of a slot blotter.

The PVDF membrane was blocked by a solution including 1 w/v % of BSA, and streptavidin-FITC (Vector Inc.) was added thereto and reacted at 37° C. for an hour.

After the reaction, the PVDF membrane was washed with 50 mM of the washing solution B three times.

After the washing, the fluorescence analysis of the PVDF membrane was conducted by means of the fluorescence image analyzer, Molecular Imager FX (Bio-Rad Laboratories, Inc.). The activity value was calculated based on the analytical curve.

The analytical curve was generated in such a manner that a solution including protein having two different concentrations (biotin-labeled immunoglobulin) was blotted on the PVDF membrane and FITC-labeled according to a method similar to that of the foregoing description so that the fluorescence intensity of the protein was measured by the fluorescence image analyzer. Therefore, the measured activity 1 U (unit) of the CDK1 refers to a value denoting the fluorescence intensity equal to the fluorescence amount in the case of 1 ng of the protein.

The activity value of the CDK2 was measured in a manner similar to that of the measurement of the activity value of the CDK1 except for using the anti-CDK2 antibody (Santa Cruz Biotechnology, Inc.) in place of the anti-CDK1 antibody.

5) Calculation of CDK Specific Activities

The CDK specific activity (mU/ng) was calculated from the CDK activity value and the CDK expression level measured earlier in the following formula.

CDK specific activity=CDK activity value/CDK expression level

The ratio between the CDK1 specific activity and the CDK2 specific activity (CDK2 specific activity/CDK1 specific activity: hereinafter, referred to as ratio of specific activities) was calculated based on the calculated CDK1 specific activity and CDK2 specific activity. The CDK1 specific activity, the CDK2 specific activity, and the ratio of specific activities are shown in the following Table 1.

6) Setting of Threshold Value and Judgment of Risk of Recurrence

The threshold value corresponding to the expression level of the cyclin E and the threshold value corresponding to the ratio of the specific activities were set. The result of the comparison of the expression level of the cyclin E to the threshold value and the result of the comparison of the ratio of the specific activities to the threshold value were combined so that the feature of the malignant tumor was judged.

The threshold value of the ratio of the specific activities was set to 46. The value is capable of separating the 129 specimen of the tumor cells obtained from 129 breast cancer patients at the ratio of 65:64 when the ratio of the specific activities in the 129 specimen of the tumor cells is calculated, and the obtained values of the ratio of the specific activities are arranged from the smaller value. "High" was judged when the value of the ratio of the specific activities was at least 46, while "Low" was judged when below 46. "Low" was judged irrespective of the ratio of the specific activities when the CDK1 specific activity was below 20 and the CDK2 specific activity was below 500. Further, "High" was judged irrespective of the ratio of the specific activities when the CDK2 specific activity was at least 10,000. The comparison result is shown in the following Table 1.

The threshold value of the expression level of the cyclin E was set to 1.7. The value was set in terms of the recurrence/non-recurrence in the patients 1-61 and the result of the comparison of the ratio of the specific activities to the threshold value. When the expression level of the cyclin E was at least 1.7, "High" was judged, and "Low" was judged when below 0.7. The comparison result is shown in the following Table 1.

The risk of recurrence was judged based on these comparison results under the following judging conditions.

The "LOW risk" of recurrence was judged when the result of the comparison of the ratio of the specific activities to the threshold value showed "Low" irrespective of the expression level of the cyclin E.

The "INTERMEDIATE risk" of recurrence was judged when the result of the comparison of the ratio of the specific activities to the threshold value showed "High", and the result of the comparison of the expression level of the cyclin E to the threshold value showed "Low".

The "HIGH risk" of recurrence was judged when the result of the comparison of the ratio of the specific activities to the threshold value showed "High", and the result of the comparison of the expression level of the cyclin E to the threshold value showed "High".

In the tumor cell judged as "LOW risk", the proliferation potency, survival potency and migratory aptitude of the cell appear to be low, and the risk of recurrence is judged as low. The tumor cell judged as "INTERMEDIATE risk" is judged as having the risk of recurrence is higher than that of the tumor cell judged as "LOW risk". The tumor cell judged as "HIGH risk" is judged as having the risk of recurrence is higher than that of the tumor cell judged as "INTERMEDIATE risk".

The Table 1 shows the judgment result of the risk of recurrence and the actual recurrence/non-recurrence. In the column of the "recurrence" in the Table, "−" denotes the "non-recurrence", and "+" denotes the "recurrence". The recurrence or non-recurrence depends on whether or not the recurrence is detected in the patients 1-51 who underwent the hormone therapy after the tumor cell blocks were extirpated from them in five years after the extirpative surgery.

TABLE 1

| patient | recurrence | expression level of cyclin E | comparison of expression level with threshold | specific activity of CDK1 | specific activity of CDK2 | ratio of specific activities | comparison of ratio with threshold | risk of recurrence |
|---|---|---|---|---|---|---|---|---|
| 1 | + | 2.066 | High | 0.0 | 1869 | ∞ | High | HIGH |
| 2 | + | 2.950 | High | 155.8 | 46513 | 298.5393 | High | HIGH |
| 3 | + | 12.561 | High | 0.0 | 2134 | ∞ | High | HIGH |
| 4 | + | 2.091 | High | 46.9 | 2534 | 54.08023 | High | HIGH |
| 5 | + | 1.890 | High | 1214.5 | 19523 | 16.07537 | High | HIGH |
| 6 | − | 0.100 | Low | 0.0 | 1299 | ∞ | High | INTERMEDIATE |
| 7 | − | 0.241 | Low | 32.1 | 1719 | 53.558 | High | INTERMEDIATE |
| 8 | − | 1.281 | Low | 0.0 | 4148 | ∞ | High | INTERMEDIATE |
| 9 | − | 0.203 | Low | 16.3 | 1676 | 102.7896 | High | INTERMEDIATE |
| 10 | − | 0.252 | Low | 19.4 | 2008 | 103.4629 | High | INTERMEDIATE |
| 11 | − | 0.235 | Low | 1.4 | 870 | 630.1985 | High | INTERMEDIATE |
| 12 | − | 0.524 | Low | 0.0 | 841 | ∞ | High | INTERMEDIATE |

TABLE 1-continued

| patient | recurrence | expression level of cyclin E | comparison of expression level with threshold | specific activity of CDK1 | specific activity of CDK2 | ratio of specific activities | comparison of ratio with threshold | risk of recurrence |
|---|---|---|---|---|---|---|---|---|
| 13 | − | 0.612 | Low | 24.8 | 5313 | 213.9562 | High | INTERMEDIATE |
| 14 | − | 1.596 | Low | 2.3 | 2143 | 950.3821 | High | INTERMEDIATE |
| 15 | + | 0.242 | Low | 108.3 | 5689 | 52.53776 | High | INTERMEDIATE |
| 16 | + | 0.767 | Low | 25.8 | 3836 | 148.6678 | High | INTERMEDIATE |
| 17 | − | 4.169 | High | 35.4 | 869 | 24.55147 | Low | LOW |
| 18 | − | 5.754 | High | 20.5 | 905 | 44.08187 | Low | LOW |
| 19 | − | 5.538 | High | 0.0 | 0 | 0 | Low | LOW |
| 20 | − | 14.714 | High | 0.0 | 0 | 0 | Low | LOW |
| 21 | − | 6.422 | High | 0.0 | 0 | 0 | Low | LOW |
| 22 | − | 2.801 | High | 296.2 | 4629 | 15.62883 | Low | LOW |
| 23 | − | 2.851 | High | 87.6 | 2409 | 27.48521 | Low | LOW |
| 24 | − | 0.495 | Low | 252.2 | 0 | 0 | Low | LOW |
| 25 | − | 0.426 | Low | 0.0 | 0 | 0 | Low | LOW |
| 26 | − | 0.623 | Low | 37.9 | 663 | 17.5067 | Low | LOW |
| 27 | − | 1.061 | Low | 191.1 | 446 | 2.324838 | Low | LOW |
| 28 | − | 0.730 | Low | 100.6 | 4597 | 45.69739 | Low | LOW |
| 29 | − | 0.321 | Low | 0.0 | 0 | 0 | Low | LOW |
| 30 | − | 0.258 | Low | 303.7 | 863 | 2.842991 | Low | LOW |
| 31 | − | 0.683 | Low | 52.4 | 509 | 9.721846 | Low | LOW |
| 32 | − | 0.244 | Low | 159.3 | 265 | 1.662478 | Low | LOW |
| 33 | − | 0.429 | Low | 179.3 | 4062 | 22.64937 | Low | LOW |
| 34 | − | 0.767 | Low | 54.6 | 2016 | 36.89663 | Low | LOW |
| 35 | − | 0.848 | Low | 0.0 | 188 | ∞ | Low | LOW |
| 36 | − | 0.765 | Low | 150.8 | 1532 | 10.16112 | Low | LOW |
| 37 | − | 0.068 | Low | 0.0 | 0 | 0 | Low | LOW |
| 38 | − | 0.117 | Low | 33.8 | 944 | 27.90448 | Low | LOW |
| 39 | − | 0.507 | Low | 0.0 | 0 | 0 | Low | LOW |
| 40 | − | 0.667 | Low | 209.3 | 0 | 0 | Low | LOW |
| 41 | − | 0.000 | Low | 123.9 | 4333 | 34.96368 | Low | LOW |
| 42 | − | 0.550 | Low | 231.0 | 3060 | 13.24827 | Low | LOW |
| 43 | − | 0.491 | Low | 152.9 | 1286 | 8.413254 | Low | LOW |
| 44 | − | 1.590 | Low | 191.6 | 4251 | 22.18577 | Low | LOW |
| 45 | − | 1.492 | Low | 15.8 | 0 | 0 | Low | LOW |
| 46 | − | 0.291 | Low | 44.3 | 0 | 0 | Low | LOW |
| 47 | − | 1.128 | Low | 39.2 | 1398 | 35.6983 | Low | LOW |
| 48 | − | 0.809 | Low | 16.9 | 167 | 9.898566 | Low | LOW |
| 49 | − | 1.081 | Low | 0.0 | 0 | 0 | Low | LOW |
| 50 | − | 0.440 | Low | 98.1 | 993 | 10.11741 | Low | LOW |
| 51 | − | 0.697 | Low | 0.0 | 0 | 0 | Low | LOW |

In the Table 1, any case where the expression level and the activity value were below a detection limit was handled as "0". Further, when the CDK1 specific activity was "0", and the CDK2 specific activity was higher than "0", the ratio of the specific activities was "infinite (∞)", which was judged as "High" in comparison to the threshold value "46" of the ratio of the specific activities. When the CDK1 specific activity and the CDK2 specific activity were both "0", the ratio of the specific activities was "0", which was judged as "Low" in comparison to the threshold value "46" of the ratio of the specific activities. Though the ratio of the specific activities is infinite in the patients 35 in the Table 1, the CDK1 specific activity was below 20, and the CDK2 specific activity was below 500; therefore, the comparison of the ratio of the specific activities to the threshold value 46 resulted in "Low".

The rate of recurrence per the risk of recurrence is shown in the following Table 2. In the Table 2, a total number of the patients having the respective risks of recurrence is shown in the column of the "number of patients", and the number of the patients whose recurrence of the malignant tumor was confirmed in these patients is shown in the column of the "number of patients whose recurrence was confirmed". In all of the five patients judged as "HIGH risk" (patients 1-5), the recurrence was detected in five years after the surgery despite the hormone therapy (rate of recurrence 100%). Of the 11 patients judged as "INTERMEDIATE risk" (patients 6-16), two of them underwent the recurrence in five years after the surgery (rate of recurrence 18%). None of the 35 patients judged as "LOW risk" (patients 17-51) experienced the recurrence in five years after the surgery (rate of recurrence 0%).

TABLE 2

| risk of recurrence | number of paitients | number of patients whose recurrence was confirmed | rate of recurrence (%) |
|---|---|---|---|
| LOW | 35 | 0 | 0 |
| INTERMEDIATE | 11 | 2 | 18 |
| HIGH | 5 | 5 | 100 |
| Total | 51 | 7 | 14 |

It can be assumed from the foregoing result that the possibility of recurrence of the malignant tumor is very high irrespective of the hormone therapy when the tumor cell judged as "HIGH risk" according to the method of the present preferred embodiment. Further, it can be assumed that the possibility of recurrence of the malignant tumor becomes very low as a result of the hormone therapy when the tumor cell judged as "LOW risk". 18%, which is the rate of recurrence when the hormone therapy is applied to the patients judged as "INTERMEDIATE risk", is substantially equal to the general rate of recurrence of the breast cancer in the early stages (10-20%).

The method according to the present preferred embodiment is particularly advantageous in that the patients, for whom the result of the comparison of the ratio of the CDK specific activities to the threshold value shows "High", can be further classified into the two groups ("HIGH risk" and "INTERMEDIATE risk") respectively having the recurrence risk at different degrees based on the result of the comparison of the expression level of the cyclin to the threshold value. As a result, the recurrence can be more accurately predicted.

Example 2

1) Preparation of Measurement Sample 76 specimen of tumor cell blocks obtained from 76 breast cancer patients (patients 1-76) classified into the stage I or the stage IIA in the breast cancer stage classification were used to prepare measurement samples 1-76 according to steps similar to those in the Working Example 1 (the stage classification of the patients are shown in the following Tables 3 and 4.)

2) Measurement of Expression Level of Cyclin B1

The expression level of the cyclin B1 was measured according to experimental steps similar to those in the measurement of the expression level of the CDK1 according to the Working Example 1 except for using not the rabbit anti-CDK1 antibody but a rabbit anti-cyclin B1 antibody (Santa Cruz Biotechnology, Inc.) specifically combined with the cyclin B1 is used as the primary antibody.

3) Measurement of Expression Levels of CDK1 and CDK2

The expression levels of the CDK1 and CDK2 were measured according to experimental steps similar to those in the measurement of the expression levels of the CDK1 and CDK2 in the Working Example 1.

4) Measurement of Activities of the CDK1 and CDK2

The activities of the CDK1 and CDK2 were measured according to experimental steps similar to those in the measurement of the activities of the CDK1 and CDK2 in the Working Example 1.

5) Calculation of CDK Specific Activities

The CDK1 specific activity, the CDK2 specific activity and the ratio of the specific activities of the CDK1 and CDK2 (ratio of specific activities) were calculated by means of the same formula as that of the calculation of the CDK specific activities in the Working Example 1.

The CDK1 specific activity, the CDK2 specific activity and the ratio of the specific activities are shown in the following Tables 3 and 4.

6) Setting of Threshold Values and Judgment of Risk of Recurrence

The threshold value corresponding to the expression level of the cyclin B1 and the threshold value corresponding to the ratio of the specific activities were set. The result of the comparison of the expression level of the cyclin B1 to the threshold value and the result of the comparison of the ratio of the specific activities to the threshold value were combined so that the feature of the malignant tumor was judged.

The threshold value of the ratio of the specific activities was set to 46. The value is capable of separating the 129 specimen of the tumor cells obtained from 129 breast cancer patients at the ratio of 65:64 when the ratio of the specific activities is calculated in the 129 specimen of the tumor cells, and the values of the ratio of the specific activities are arranged from the smaller value. "High" was judged when the value of the ratio of the specific activities is at least 46, while "Low" was judged when below 46. "Low" was judged irrespective of the ratio of the specific activities when the CDK1 specific activity was below 20 and the CDK2 specific activity is below 500. Further, "High" was judged irrespective of the ratio of the specific activities when the CDK2 specific activity was at least 10,000. The comparison result is shown in the following Tables 3 and 4.

The threshold value of the expression level of the cyclin B1 was set to 0.0195. The value was set in terms of the recurrence non-recurrence in the patients 1-76 and the result of the comparison of the ratio of the specific activities to the threshold value. "High" was judged when the expression level of the cyclin B1 was at least 0.0195, and "Low" was judged when below 0.0195. The comparison result is shown in the following Tables 3 and 4.

The risk of recurrence was judged based on these comparison results under the following judging conditions.

The "LOW risk" of recurrence was judged when the result of the comparison of the ratio of the specific activities to the threshold value showed "Low", and the result of the comparison of the expression level of the cyclin B1 to the threshold value showed "Low".

The "INTERMEDIATE risk" of recurrence was judged when the result of the comparison of the ratio of the specific activities to the threshold value showed "High", and the result of the comparison of the expression level of the cyclin B1 to the threshold value showed "Low". The "INTERMEDIATE risk" of recurrence was also judged when the result of the comparison of the ratio of the specific activities to the threshold value showed "Low", and the result of the comparison of the expression level of the cyclin B1 to the threshold value showed "High".

The "HIGH risk" of recurrence was judged when the result of the comparison of the ratio of the specific activities to the threshold value showed "High", and the result of the comparison of the expression level of the cyclin B1 to the threshold value showed "High".

In the tumor cell judged as "LOW risk", the proliferation potency, survival potency and migratory aptitude of the cell appear to be low, and the risk of recurrence is judged as low. The tumor cell judged as "INTERMEDIATE risk" is judged as having the risk of recurrence is higher than that of the tumor cell judged as "LOW risk". The tumor cell judged as "HIGH risk" is judged as having the risk of recurrence is higher than that of the tumor cell judged as "INTERMEDIATE risk".

The Tables 3 and 4 show the judgment result of the risk of recurrence and the actual recurrence/non-recurrence. In the column of the "recurrence" in the Table, "−" denotes the "non-recurrence", and "+" denotes the "recurrence". The recurrence or non-recurrence depends on whether or not the recurrence was detected in the patients 1-76 who underwent the hormone therapy or did not receive any therapy after the tumor cell blocks were extirpated from them in five years after the extirpative surgery.

TABLE 3

| patient | recurrence | expression level of cyclin B1 | comparison of expression level with threshold | specific activity of CDK1 | specific activity of CDK2 | ratio of specific activities | comparison of ratio with threshold | risk of recurrence |
|---|---|---|---|---|---|---|---|---|
| 1 | + | 0.04541 | High | 176.50359 | 10179.57242 | 57.67346 | High | HIGH |
| 2 | + | 0.04107 | High | 46.85581 | 2533.91281 | 54.08023 | High | HIGH |
| 3 | − | 0.03589 | High | 0 | 841.38124 | ∞ | High | HIGH |
| 4 | + | 0.03502 | High | 0 | 2133.95331 | ∞ | High | HIGH |
| 5 | − | 0.03322 | High | 31.41812 | 5103.06498 | 162.58340 | High | HIGH |
| 6 | − | 0.03023 | High | 24.83021 | 5312.51824 | 213.95621 | High | HIGH |
| 7 | − | 0.02793 | High | 1.38070 | 870.11784 | 630.19848 | High | HIGH |
| 8 | + | 0.02689 | High | 108.28745 | 5689.17972 | 52.53776 | High | HIGH |
| 9 | + | 0.02671 | High | 155.80197 | ∞ | ∞ | High | HIGH |
| 10 | + | 0.02586 | High | 1214.46645 | 19522.99602 | 16.07537 | High | HIGH |
| 11 | + | 0.02218 | High | 25.80227 | 3835.96673 | 148.66781 | High | HIGH |
| 12 | − | 0.02157 | High | 19.41183 | 2008.40442 | 103.46291 | High | HIGH |
| 13 | + | 0.02098 | High | 169.00953 | ∞ | ∞ | High | HIGH |
| 14 | − | 0.02028 | High | 16.02857 | 2465.61777 | 153.82644 | High | HIGH |
| 15 | + | 0.01985 | High | 0 | 1869.29070 | ∞ | High | HIGH |
| 16 | − | 0.01928 | Low | 16.59366 | 3065.34083 | 184.72969 | High | INTERMEDIATE |
| 17 | − | 0.01770 | Low | 0 | 4148.04356 | ∞ | High | INTERMEDIATE |
| 18 | − | 0.01492 | Low | 0 | 1091.10461 | ∞ | High | INTERMEDIATE |
| 19 | − | 0.01481 | Low | 32.09491 | 1718.93943 | 53.55800 | High | INTERMEDIATE |
| 20 | − | 0.01372 | Low | 16.30544 | 1676.02894 | 102.78957 | High | INTERMEDIATE |
| 21 | − | 0.01352 | Low | 0 | 1298.86187 | ∞ | High | INTERMEDIATE |
| 22 | + | 0.00821 | Low | 0 | ∞ | ∞ | High | INTERMEDIATE |
| 23 | − | 0.13871 | High | 98.14011 | 992.92383 | 10.11741 | Low | INTERMEDIATE |
| 24 | − | 0.06268 | High | 114.42248 | 0 | 0 | Low | INTERMEDIATE |
| 25 | − | 0.05743 | High | 57.87807 | 0 | 0 | Low | INTERMEDIATE |
| 26 | − | 0.05531 | High | 0 | 0 | 0 | Low | INTERMEDIATE |
| 27 | − | 0.05517 | High | 0 | 0 | 0 | Low | INTERMEDIATE |
| 28 | − | 0.04794 | High | 421.96126 | 8581.66038 | 20.33155 | Low | INTERMEDIATE |
| 29 | − | 0.04376 | High | 85.91934 | 732.34735 | 8.52366 | Low | INTERMEDIATE |
| 30 | − | 0.03870 | High | 0 | 0 | 0 | Low | INTERMEDIATE |
| 31 | − | 0.03544 | High | 190.13758 | 3775.30139 | 19.85563 | Low | INTERMEDIATE |
| 32 | − | 0.03492 | High | 0 | 0 | 0 | Low | INTERMEDIATE |
| 33 | − | 0.03128 | High | 123.93678 | 4333.28586 | 34.96368 | Low | INTERMEDIATE |
| 34 | − | 0.02883 | High | 52.38498 | 509.27877 | 9.72185 | Low | INTERMEDIATE |
| 35 | − | 0.02631 | High | 33.83529 | 944.15610 | 27.90448 | Low | INTERMEDIATE |
| 36 | − | 0.02565 | High | 87.63474 | 2408.65926 | 27.48521 | Low | INTERMEDIATE |
| 37 | − | 0.02483 | High | 152.90697 | 1286.44512 | 8.41325 | Low | INTERMEDIATE |
| 38 | − | 0.02371 | High | 51.42980 | 1234.42935 | 24.00222 | Low | INTERMEDIATE |

TABLE 4

| patient | recurrence | expression level of cyclin B1 | comparison of expression level with threshold | specific activity of CDK1 | specific activity of CDK2 | ratio of specific activities | comparison of ratio with threshold | risk of recurrence |
|---|---|---|---|---|---|---|---|---|
| 39 | − | 0.02180 | High | 176.71590 | 6192.48701 | 35.04206 | Low | INTERMEDIATE |
| 40 | − | 0.02155 | High | 20.52354 | 904.71593 | 44.06187 | Low | INTERMEDIATE |
| 41 | − | 0.02141 | High | 13.94306 | 601.71022 | 43.15483 | Low | INTERMEDIATE |
| 42 | − | 0.02044 | High | 39.15167 | 1397.64821 | 35.69830 | Low | INTERMEDIATE |
| 43 | − | 0.02037 | High | 15.19414 | 0 | 0 | Low | INTERMEDIATE |
| 44 | + | 0.01953 | High | 18.61619 | 0 | 0 | Low | INTERMEDIATE |
| 45 | − | 0.01946 | Low | 230.98749 | 3060.18486 | 13.24827 | Low | LOW |
| 46 | − | 0.01935 | Low | 25.65663 | 0 | 0 | Low | LOW |
| 47 | − | 0.01925 | Low | 0 | 0 | 0 | Low | LOW |
| 48 | − | 0.01912 | Low | 35.40095 | 869.14539 | 24.55147 | Low | LOW |
| 49 | − | 0.01840 | Low | 191.67842 | 445.62122 | 2.32484 | Low | LOW |
| 50 | − | 0.01782 | Low | 0 | 0 | 0 | Low | LOW |
| 51 | − | 0.01739 | Low | 37.85326 | 662.64792 | 17.50670 | Low | LOW |
| 52 | − | 0.01735 | Low | 191.61616 | 4251.15167 | 22.18577 | Low | LOW |
| 53 | − | 0.01734 | Low | 296.19120 | 4629.12075 | 15.62883 | Low | LOW |
| 54 | − | 0.01682 | Low | 0 | 0 | 0 | Low | LOW |
| 55 | − | 0.01677 | Low | 26.98432 | 902.53753 | 33.44674 | Low | LOW |
| 56 | − | 0.01615 | Low | 0 | 0 | 0 | Low | LOW |
| 57 | − | 0.01615 | Low | 54.63500 | 2015.84718 | 36.89663 | Low | LOW |
| 58 | − | 0.01497 | Low | 0 | 187.69165 | ∞ | Low | LOW |
| 59 | − | 0.01478 | Low | 0 | 0 | 0 | Low | LOW |
| 60 | − | 0.01469 | Low | 150.77813 | 1532.07394 | 10.16112 | Low | LOW |
| 61 | − | 0.01440 | Low | 159.30846 | 264.84676 | 1.66248 | Low | LOW |
| 62 | − | 0.01412 | Low | 285.45529 | 4604.22420 | 16.12941 | Low | LOW |
| 63 | − | 0.01399 | Low | 216.20425 | 6239.16828 | 28.85775 | Low | LOW |
| 64 | − | 0.01397 | Low | 0 | 0 | 0 | Low | LOW |
| 65 | − | 0.01332 | Low | 179.32800 | 4061.66649 | 22.64931 | Low | LOW |
| 66 | − | 0.01285 | Low | 16.86012 | 166.89101 | 9.89857 | Low | LOW |
| 67 | − | 0.01195 | Low | 0 | 0 | 0 | Low | LOW |
| 68 | − | 0.01184 | Low | 252.21810 | 0 | 0 | Low | LOW |

TABLE 4-continued

| | | | | | | | | |
|---|---|---|---|---|---|---|---|---|
| 69 | – | 0.01179 | Low | 0 | 0 | 0 | Low | LOW |
| 70 | – | 0.01168 | Low | 302.65537 | 863.28933 | 2.84299 | Low | LOW |
| 71 | – | 0.01143 | Low | 0 | 0 | 0 | Low | LOW |
| 72 | – | 0.01071 | Low | 0 | 0 | 0 | Low | LOW |
| 73 | – | 0.00829 | Low | 68.96305 | 1332.02803 | 19.31510 | Low | LOW |
| 74 | – | 0.00716 | Low | 188.47428 | 0 | 0 | Low | LOW |
| 75 | – | 0.00631 | Low | 100.59602 | 4596.97529 | 45.69739 | Low | LOW |
| 76 | – | 0.00629 | Low | 116.35529 | 2789.75360 | 23.97616 | Low | LOW |

In the Tables 3 and 4, any case where the expression level and the activity value were below a detection limit was handled as "0". Further, when the CDK1 specific activity was "0", and the CDK2 specific activity was higher than "0", the ratio of the specific activities was "infinite (∞)", which was judged as "High" in comparison to the threshold value "46" of the ratio of the specific activities. When the CDK1 specific activity and the CDK2 specific activity were both "0", the ratio of the specific activities was "0", which was judged as "Low" in comparison to the threshold value "46" of the ratio of the specific activities. Though the ratio of the specific activities is infinite in the patients 58 in the Table 4, the CDK1 specific activity was below 20, and the CDK2 specific activity was below 500; therefore, the comparison of the ratio of the specific activities to the threshold value 46 resulted in "Low".

The rate of recurrence per the risk of recurrence is shown in the following Table 5. In the Table 5, a total number of the patients having the respective risks of recurrence is shown in the column of the "number of patients", and the number of the patients whose recurrence of the malignant tumor was confirmed in these patients is shown in the column of the "number of patients whose recurrence was confirmed". Of all of the 15 patients judged as "HIGH risk" (patients 1-15), the recurrence was detected in nine patients in five years after the surgery despite the hormone therapy (rate of recurrence 60%). The rate of recurrence in the case of providing the hormone therapy for the patients judged as "HIGH risk", which is 60%, is equal to the rate of recurrence in the breast cancer patients classified into the stage III in the stage classification. Of the 29 patients judged as "INTERMEDIATE risk" (patients 16-44), two of them underwent the recurrence in five years after the surgery (rate of recurrence (6.9%). Of these two patients, the patient 22 was classified into the "Low" according to the result of the comparison of the ratio of the specific activities to the threshold value, and the patient 44 was classified into the "Low" according to the result of the comparison of the expression level of the cyclin B1 to the threshold value. None of the 32 patients judged as "LOW risk" (patients 45-76) experienced the recurrence in five years after the surgery (rate of recurrence 0%).

TABLE 5

| risk of recurrence | number of paitients | number of patients whose recurrence was confirmed | rate of recurrence (%) |
|---|---|---|---|
| LOW | 32 | 0 | 0.0 |
| INTERMEDIATE | 29 | 2 | 6.9 |
| HIGH | 15 | 9 | 60.0 |
| Total | 76 | 11 | 14.5 |

It can be assumed from the foregoing result that the possibility of recurrence of the malignant tumor is very high irrespective of the hormone therapy when the tumor cell judged as "HIGH risk" according to the method of the present preferred embodiment. Further, it can be assumed that the possibility of recurrence of the malignant tumor becomes very low as a result of the hormone therapy when the tumor cell judged as "LOW risk".

The method according to the present preferred embodiment is particularly advantageous in that, of the patients classified into the "Low" according to each comparison result, those who possibly undergo the recurrence can be classified into "INTERMEDIATE risk" when the result of the comparison of the ratio of the CDK specific activities to the threshold value and the result of the comparison of the expression level of the cyclin to the threshold value are combined. As a result, the recurrence can be more accurately predicted.

The result of the prediction of the risk of recurrence thus far described is useful as an indicator for judging a therapeutic policy for the patients having the malignant tumor. For example, for those who were judged as "HIGH risk", an aggressive therapy (for example, chemotherapy) can be selected. For those who were judged as having the "INTERMEDIATE risk", various other factors (for example, age, nucleus heteromorphism, diameter of tumor, and the like) are comprehensively examined when the therapeutic policy is selected. Further, it can be known that the recurrence can be controlled at a high rate by the hormone therapy in place of the chemotherapy exerting strong side effects and causing a heavy economic burden when the risk of recurrence is judged to be "LOW risk".

What is claimed is:

1. A computer-implemented method for judging a risk of recurrence of breast cancer, comprising steps of:
    obtaining a ratio of a specific activity for cyclin dependent kinase 1 (CKD1) and a specific activity for CDK2, and an expression level of at least one cyclin selected from the group consisting of cyclin B1 and cyclin E contained in a tumor cell of the breast cancer, wherein the CDK1 specific activity is a ratio of an activation value of the CDK1 and an expression level of the CDK1 contained in the tumor cell, and the CDK2 specific activity is a ratio of an activation value of the CDK2 and an expression level of the CDK2 contained in the tumor cell;
    first comparing a first threshold value stored in a memory with the ratio of the CDK1 specific activity and the CDK2 specific activity;
    second comparing a second threshold value stored in the memory with the expression level of the cyclin;
    judging a risk level of recurrence of breast cancer, on the basis of the first comparison result, the second comparison result and risk information which represents relationship of risk levels, a ratio of CDCK1 specific activity and CDK2 specific activity, and a expression level of the cyclin, and is stored in the memory;
    wherein each method step is executed by a computer processor.

2. The method according to claim 1, wherein the cyclin is capable of forming a complex with at least one CDK selected from the group consisting of CDK1, CDK2, CDK4 and CDK6.

3. The method according to claim 2, wherein the cyclin is selected from the group consisting of cyclin A, cyclin B, cyclin D and cyclin E.

4. The method according to claim 3, wherein the cyclin is cyclin B or cyclin E.

5. The method according to claim 1, wherein
the judging step is performed so as to judge the risk of recurrence as high risk, intermediate risk or low risk, based on the first comparison result and the second comparison.

6. The method according to claim 5, wherein
the low risk is determined when the ratio of the CDK1 specific activity and the CDK2 specific activity is less than the first threshold value,
the intermediate risk is determined when the ratio of the CDK1 specific activity and the CDK2 specific activity is not less than the first threshold value and the expression level of the cyclin is less than the second threshold value, and
the high risk is determined when the ratio of the CDK1 specific activity and the CDK2 specific activity is not less than the first threshold value and the expression level of the cyclin is not less than the second threshold value.

7. The method according to claim 5, wherein
the low risk is determined when the ratio of the CDK1 specific activity and the CDK2 specific activity is less than the first threshold value and the expression level of the cyclin is less than the second threshold value,
the intermediate risk is determined when the ratio of the CDK1 specific activity and the CDK2 specific activity is not less than the first threshold value and the expression level of the cyclin is less than the second threshold value and when the ratio of the CDK1 specific activity and the CDK2 specific activity is less than the first threshold value and the expression level of the cyclin is not less than the second threshold value, and
the high risk is determined when the ratio of the CDK1 specific activity and the CDK2 specific activity is not less than the first threshold value and the expression level of the cyclin is not less than the second threshold value.

8. The method according to claim 1, wherein the malignant tumor belongs to Stage I or Stage IIA in stage classification.

9. A method for judging risk of recurrence of breast cancer, comprising:
obtaining a ratio of a specific activity for cyclin dependent kinase 1 (CDK1) and a specific activity for CDK2, and an expression level of at least one cyclin selected from the group consisting of cyclin B1 and cyclin E contained in a tumor cell of the breast cancer, wherein the CDK1 specific activity is a ratio of an activation value of the CDK1 and an expression level of the CDK1 contained in the tumor cell, and the CDK2 specific activity for the CDK2 is a ratio of an activation value of the CDK2 and an expression level of the CDK2 contained in the tumor cell;
first comparing a first threshold value stored in a memory with ratio of the CDK1 specific activity and the CDK2 specific activity;
first classifying the breast cancer into one of Group A and Group X having a risk of recurrence higher than that of the Group A based on the first comparison result;
second comparing a second threshold value stored in the memory with the expression level of the at least one cyclin when it is judged that the breast cancer is included in the Group X; and
second classifying the Group X into Group B and Group C having the risk of recurrence higher than that of the Group B based on the second comparison result;
wherein each method step is executed by a computer processor.

10. A computer product comprising a computer-recordable medium having stored thereon instructions to enable a computer to perform a process for judging the risk of recurrence of breast cancer, the instructions comprising:
obtaining a ratio of a specific activity for cyclin dependent kinase 1 (CDK1) and a specific activity for CDK2, and an expression level of at least one cyclin selected from the group consisting of cyclin B1 and cyclin E contained in a tumor cell of the breast cancer, wherein the CDK1 specific activity is a ratio of an activation value of the CDK1 and an expression level of the CDK1 contained in the tumor cell, and the CDK2 specific activity is the ration of an activation value of the CDK2 and an expression level of the CDK2 contained in the tumor cell;
first comparing a first threshold value stored in a memory with the ratio of the CDK1 specific activity and the CDK2 specific activity;
second comparing a second threshold value stored in the memory with the expression level of cyclin;
judging a risk level of recurrence of breast cancer, on the basis of the first comparison result, the second comparison result and risk information which represents relations of first levels, a ratio of CDK1 specific activity and CDK2 specific activity, and a expression level of the cyclin, and is stored in the memory;
wherein the computer-readable media is non-transitory.

11. The computer-recordable medium according to claim 10, wherein the judging step is performed so as to judge the risk of recurrence as high risk, intermediate risk or low risk, based on the first comparison result, and the second comparison result.

* * * * *